United States Patent
Okaguchi

(10) Patent No.: US 12,092,094 B2
(45) Date of Patent: Sep. 17, 2024

(54) FLUID CONTROL DEVICE AND SPHYGMOMANOMETER

(71) Applicant: Murata Manufacturing Co., Ltd., Kyoto (JP)

(72) Inventor: Kenjiro Okaguchi, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 1405 days.

(21) Appl. No.: 16/569,923

(22) Filed: Sep. 13, 2019

(65) Prior Publication Data

US 2020/0000346 A1 Jan. 2, 2020

Related U.S. Application Data

(63) Continuation of application No. PCT/JP2018/006384, filed on Feb. 22, 2018.

(30) Foreign Application Priority Data

Mar. 16, 2017 (JP) .................. 2017-051215

(51) Int. Cl.
*F04B 45/047* (2006.01)
*A61B 5/0225* (2006.01)
(Continued)

(52) U.S. Cl.
CPC .......... *F04B 45/047* (2013.01); *A61B 5/0225* (2013.01); *F04B 49/02* (2013.01); *H02N 2/06* (2013.01); *H03B 5/32* (2013.01)

(58) Field of Classification Search
CPC ........ F04B 45/047; F04B 49/02; F04B 53/22; F04B 49/10; F04B 2205/05;
(Continued)

(56) References Cited

U.S. PATENT DOCUMENTS 4,268,807 A * 5/1981 Spence .................. H03H 11/54
333/191
5,047,731 A * 9/1991 Lee ....................... H03F 3/3435
330/307
(Continued)

FOREIGN PATENT DOCUMENTS

CN 104254276 A 12/2014
JP H02-119984 U 9/1990
(Continued)

OTHER PUBLICATIONS

International Search Report for International Application No. PCT/JP2018/006384 dated May 15, 2018.
(Continued)

*Primary Examiner* — Emily P Pham
(74) *Attorney, Agent, or Firm* — Pearne & Gordon LLP

(57) ABSTRACT

A fluid control device includes a piezoelectric pump that includes a piezoelectric element and whose discharge pressure output varies depending on a drive frequency of the piezoelectric element, a self oscillation circuit that self-oscillates in accordance with a drive supply voltage and that drives the piezoelectric element at an oscillation frequency, and a control circuit that generates a control voltage. The oscillation frequency of the self oscillation circuit varies depending on the control voltage.

14 Claims, 8 Drawing Sheets

(51) Int. Cl.
*F04B 49/02* (2006.01)
*H02N 2/06* (2006.01)
*H03B 5/32* (2006.01)

(58) Field of Classification Search
CPC .......... A61B 5/0225; H02N 2/06; H03B 5/32; H10N 30/802; H03H 11/04
See application file for complete search history.

(56) References Cited

U.S. PATENT DOCUMENTS

| | | | |
|---|---|---|---|
| 9,711,706 B2 * | 7/2017 | Okaguchi | H10N 30/802 |
| 11,773,835 B2 * | 10/2023 | Okaguchi | F04B 49/08 |
| | | | 600/490 |
| 2004/0066244 A1 * | 4/2004 | Takinami | H03B 5/1228 |
| | | | 331/117 R |
| 2011/0068657 A1 | 3/2011 | Sunaga et al. | |
| 2012/0220884 A1 * | 8/2012 | Yamashita | A61B 5/022 |
| | | | 600/490 |
| 2014/0257116 A1 * | 9/2014 | Kobayashi | A61B 5/022 |
| | | | 600/490 |
| 2014/0276146 A1 | 9/2014 | Yamashita et al. | |
| 2014/0309541 A1 * | 10/2014 | Yamashita | A61B 5/02233 |
| | | | 600/485 |
| 2015/0038858 A1 | 2/2015 | Ariga et al. | |
| 2017/0126148 A1 | 5/2017 | Okaguchi | |
| 2018/0132732 A1 * | 5/2018 | Lin | F04B 19/006 |
| 2018/0309391 A1 * | 10/2018 | Endou | B06B 1/0269 |
| 2020/0367770 A1 * | 11/2020 | Lin | F04B 45/047 |

FOREIGN PATENT DOCUMENTS

| | | |
|---|---|---|
| JP | 2010-142783 A | 7/2010 |
| JP | 2011-87455 A | 4/2011 |
| JP | 2013-220288 A | 10/2013 |
| WO | 2013/084579 A1 | 6/2013 |
| WO | 2016/009869 A1 | 1/2016 |

OTHER PUBLICATIONS

Written Opinion for International Application No. PCT/JP2018/006384 dated May 15, 2018.

* cited by examiner

FLUID CONTROL DEVICE AND SPHYGMOMANOMETER

This is a continuation of International Application No. PCT/JP2018/006384 filed on Feb. 22, 2018 which claims priority from Japanese Patent Application No. 2017-051215 filed on Mar. 16, 2017. The contents of these applications are incorporated herein by reference in their entireties.

BACKGROUND

Technical Field

The present disclosure relates to a fluid control device and a sphygmomanometer. The fluid control device includes a piezoelectric pump, and the sphygmomanometer includes this fluid control device.

A fluid control device disclosed in Patent Document 1 is an example of fluid control devices of the related art. The fluid control device includes a piezoelectric pump and a voltage output driver. The piezoelectric pump includes a piezoelectric element, and the voltage output driver outputs a drive voltage to the piezoelectric element. The voltage output driver includes a voltage booster circuit, a digital/analog (D/A) converter, and an amplifier circuit. The voltage booster circuit boosts a low voltage in a signal source and generates a high voltage in a drive power supply. The D/A converter generates a drive waveform for the piezoelectric element, and the amplifier circuit amplifies the drive waveform for the piezoelectric element by using the drive power supply as the power source. In this configuration, the drive voltage for driving the piezoelectric element is generated and applied to the piezoelectric element.

Patent Document 1: Japanese Unexamined Patent Application Publication No. 2010-142783

BRIEF SUMMARY

A fluid control device is used, for example, for a sphygmomanometer for a newborn baby. A small-volume cuff is used for a sphygmomanometer for a newborn baby, and if the pressurizing rate of a piezoelectric pump is too fast, the cuff is instantly filled with air. Accordingly, the piezoelectric pump needs to slowly discharge air into the cuff. Thus, the piezoelectric pump needs to be operable in a low output range of discharge pressure.

The voltage output driver disclosed in Patent Document 1 amplifies a drive waveform for the piezoelectric element by using a high-voltage drive power supply as the power source and thus generates a drive voltage for driving the piezoelectric element. Consequently, a drive voltage having a small amplitude cannot be obtained and controlling the amplitude and the frequency of a drive voltage with high accuracy is difficult. As a result, operating the piezoelectric pump in a low output range of discharge pressure is difficult.

The present disclosure provides a fluid control device in which a piezoelectric pump is operable in a low output range of discharge pressure and a sphygmomanometer that includes the fluid control device.

(1) A fluid control device according to the present disclosure includes a piezoelectric pump that includes a piezoelectric element and whose discharge pressure output varies depending on a drive frequency of the piezoelectric element, and the fluid control device also includes a self oscillation circuit that self-oscillates in accordance with a drive supply voltage and that drives the piezoelectric element at an oscillation frequency. The fluid control device further includes a control circuit that generates a control voltage, and the oscillation frequency of the self oscillation circuit varies depending on the control voltage. In this configuration, the drive frequency of the piezoelectric element equals the oscillation frequency of the self oscillation circuit. The oscillation frequency of the self oscillation circuit varies depending on the control voltage and shifts from the resonant frequency of the piezoelectric element. Consequently, the piezoelectric pump operates in a low output range of the discharge pressure.

(2) An input-output phase difference generated from an input signal and an output signal used for driving the piezoelectric pump can vary as the control voltage varies. Consequently, the piezoelectric pump operates in a low output range of the discharge pressure.

(3) The self oscillation circuit can include a filter circuit, the filter circuit can include a variable impedance unit whose impedance varies depending on the control voltage, and bandpass characteristics of the filter circuit can change as the impedance of the variable impedance unit varies. In this configuration, the bandpass characteristics of the filter circuit change depending on the control voltage, and thus the oscillation frequency of the self oscillation circuit varies.

(4) The variable impedance unit can have resistance or capacitance that varies depending on the control voltage. In this configuration, resistance or capacitance varies depending on the control voltage, leading to a change in the bandpass characteristics of the filter circuit.

(5) The variable impedance unit may include a field effect transistor (FET), and the control voltage may be applied to the gate of the FET. In this configuration, the control voltage determines the resistance between the drain and the source of the FET.

(6) The variable impedance unit may include a variable capacitance element, and the control voltage may be applied to the variable capacitance element. In this configuration, the control voltage determines the capacitance of the variable capacitance element.

(7) The filter circuit can include at least one of a band pass filter and a low pass filter. In this configuration, the control voltage determines the bandpass characteristics of at least one of the band pass filter and the low pass filter.

(8) The piezoelectric pump can have a first low-output region and a first high-output region as predetermined output ranges of discharge pressure. An upper limit of the first high-output region is higher than an upper limit of the first low-output region, and a lower limit of the first high-output region is higher than a lower limit of the first low-output region. The control circuit can control the drive supply voltage, can vary in the first low-output region the control voltage while maintaining the drive supply voltage at a fixed level, and can vary in the first high-output region the drive supply voltage while maintaining the control voltage at a fixed level. In this configuration, the dynamic range of the piezoelectric pump is enlarged. Further, the discharge pressure output of the piezoelectric pump can continuously be varied in the entire output range of the discharge pressure of the piezoelectric pump.

(9) The piezoelectric pump may have a second low-output region and a second high-output region as predetermined output ranges of discharge pressure. An upper limit of the second high-output region is higher than an upper limit of the second low-output region, and a lower limit of the second high-output region is higher than a lower limit of the second low-output region. The self oscillation circuit may drive the piezoelectric element by using an unbalanced signal in the second low-output region and may drive the piezoelectric element by using a balanced signal in the second high-output region.

In this configuration, since the piezoelectric element is driven by using an unbalanced signal, the piezoelectric pump operates in a low output range of the discharge pressure. Further, since the drive based on a balanced signal and the drive based on an unbalanced signal are switched in accordance with the output range of the discharge pressure of the piezoelectric pump, the dynamic range of the piezoelectric pump is enlarged. In addition, since the piezoelectric element can be driven at a frequency approximately equal to the resonant frequency of the piezoelectric element in the entire output range of the discharge pressure of the piezoelectric pump, the efficiency of the fluid control device can be improved. Consequently, if the power supply of the fluid control device is constituted by a battery, the life of the battery can be extended.

(10) A sphygmomanometer according to the present disclosure includes a cuff and a fluid control device that pressurizes the cuff. The fluid control device includes a piezoelectric pump that includes a piezoelectric element and whose discharge pressure output varies depending on a drive frequency of the piezoelectric element, and the fluid control device also includes a self oscillation circuit that self-oscillates in accordance with a drive supply voltage and that drives the piezoelectric element at an oscillation frequency. The fluid control device further includes a control circuit that generates a control voltage, and the oscillation frequency of the self oscillation circuit varies depending on the control voltage. In this configuration, as described above, the piezoelectric pump is operable in a low output range of discharge pressure. Consequently, an accurate blood pressure measurement is possible when the sphygmomanometer according to the present disclosure is used, for example, for a newborn baby.

According to the present disclosure, a fluid control device in which a piezoelectric pump is operable in a low output range of discharge pressure and a sphygmomanometer that includes the fluid control device can be realized.

DETAILED DESCRIPTION

Figure 1:
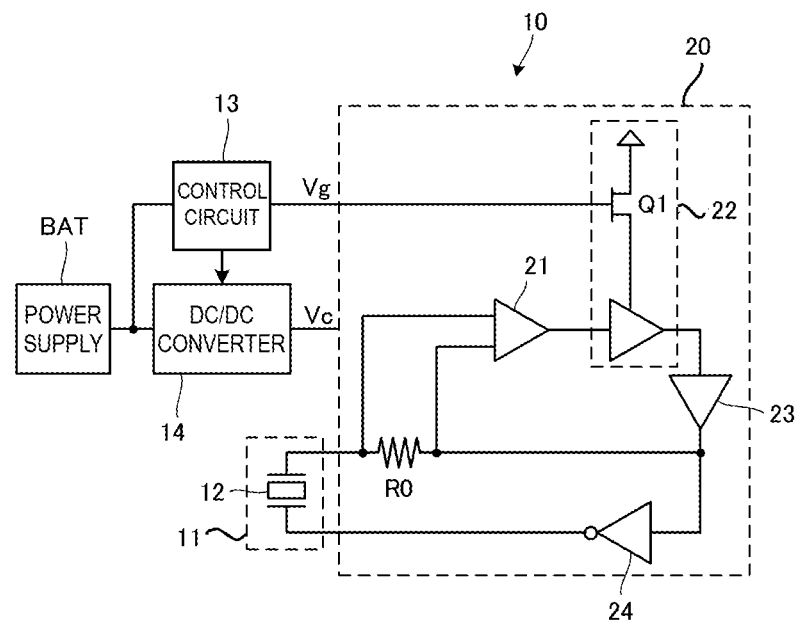
FIG. 1 is a block diagram illustrating a configuration of a fluid control device 10 according to a first embodiment.

Hereinafter, several specific examples will be described with reference to the drawings, and a plurality of embodiments to carry out the present disclosure will be described. In the drawings, like portions are denoted by like numerals or symbols. Although embodiments will be described separately as appropriate in consideration of the easiness of describing or understanding main features, partial substitutions and combinations of configurations illustrated in different embodiments can be made. In a second embodiment and subsequent embodiments, features common to a first embodiment will not be described, and only different features will be described. In particular, similar operations and advantages achievable by similar configurations will not individually be described in each of the embodiments.

First Embodiment

FIG. 1 is a block diagram illustrating a configuration of a fluid control device 10 according to a first embodiment. The fluid control device 10 includes a piezoelectric pump 11, a self oscillation circuit 20, a control circuit 13, and a direct current to direct current (DC/DC) converter 14. The fluid control device 10 and the control circuit 13 are powered by a power supply BAT.

The piezoelectric pump 11 includes a piezoelectric element 12. The discharge pressure output of the piezoelectric pump 11 varies depending on the drive frequency of the piezoelectric element 12. The self oscillation circuit 20 self-oscillates in accordance with a drive supply voltage Vc. The self oscillation circuit 20 drives the piezoelectric element 12 at an oscillation frequency fe. Namely, the drive frequency of the piezoelectric element 12 is equal to the oscillation frequency fe of the self oscillation circuit 20. The oscillation frequency fe of the self oscillation circuit 20 varies depending on a control voltage Vg. For example, the range of variation of the oscillation frequency fe is set to fr−1 kHz or more and fr+1 kHz or less, where fr is the resonant frequency of the piezoelectric element 12. The DC/DC converter 14 boosts or steps down the voltage of the power supply BAT and provides the self oscillation circuit 20 with the drive supply voltage Vc. The control circuit 13 generates the control voltage Vg. The control circuit 13 controls the drive supply voltage Vc. Specifically, the control circuit 13 sets the drive supply voltage Vc, for example, by controlling the ON duty ratio of a switching element (not shown) in the DC/DC converter 14. The control circuit 13 varies the control voltage Vg and the drive supply voltage Vc in predetermined ranges of variation. The control circuit 13 is constituted by a micro control unit (MCU) or the like. A pulse-width modulation (PWM) signal generated by the MCU, a signal obtained by smoothing the PWM signal, or the like is used as the control voltage Vg.

The self oscillation circuit 20 is constituted as a positive feedback circuit that satisfies the Barkhausen condition for oscillation. The self oscillation circuit 20 includes a resistor for detecting output current R0, a differential amplifier circuit having a low pass filter (LPF) (hereinafter referred to as an LPF differential amplifier circuit) 21, an amplifier circuit having a band pass filter (BPF) (hereinafter referred to as a BPF amplifier circuit) 22, a comparator 23, and an inverting comparator 24. The BPF amplifier circuit 22 is an example of a "filter circuit" and a "band pass filter" according to the present disclosure. Two input terminals of the LPF differential amplifier circuit 21 are individually connected to each of the two ends of the resistor for detecting output current R0. The output terminal of the LPF differential amplifier circuit 21 is connected to the input terminal of the BPF amplifier circuit 22. The output terminal of the BPF amplifier circuit 22 is connected to the input terminal of the comparator 23. The output terminal of the comparator 23 is connected through the resistor for detecting output current R0 to a first end of the piezoelectric element 12 and also connected to the input terminal of the inverting comparator 24. The output terminal of the inverting comparator 24 is connected to a second end of the piezoelectric element 12. The BPF amplifier circuit 22 includes a transistor Q1 (n-channel metal-oxide-semiconductor field effect transistor (MOS-FET)). The transistor Q1 is an example of a "variable impedance unit" of the present disclosure. The control circuit 13 applies the control voltage Vg to the gate of the transistor Q1.

The LPF differential amplifier circuit 21 suppresses or reduces harmonic components in a voltage drop across the resistor for detecting output current R0 and differentially amplifies the voltage drop across the resistor for detecting output current R0. The BPF amplifier circuit 22 amplifies a frequency component having the oscillation frequency fe in the output voltage of the LPF differential amplifier circuit 21 and suppresses or reduces other unnecessary frequency components. The comparator 23 having a single input converts the output voltage of the BPF amplifier circuit 22 into a binary voltage signal. The inverting comparator 24 inverts the phase (polarity) of the output voltage of the comparator 23. The output voltage of the comparator 23 is input through the resistor for detecting output current R0 to the first end of the piezoelectric element 12, and the output voltage of the inverting comparator 24 is input to the second end of the piezoelectric element 12. An alternating voltage having the oscillation frequency fe of the self oscillation circuit 20 is applied to the piezoelectric element 12 by using the above circuit configuration.

Figure 2:
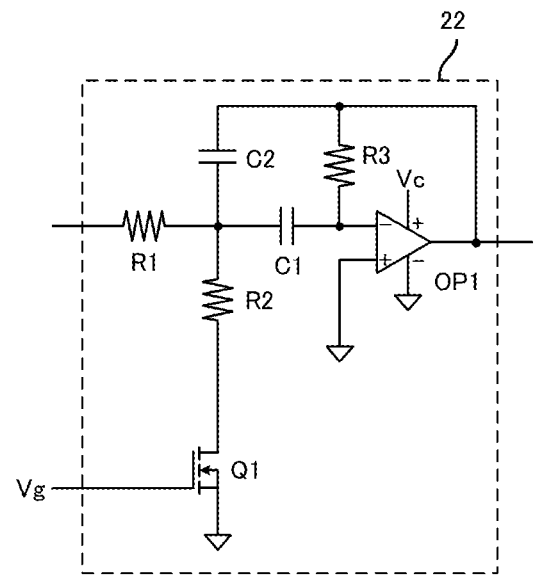
FIG. 2 is a circuit diagram of an amplifier circuit having a band pass filter (BPF) 22.

FIG. 2 is a circuit diagram of the BPF amplifier circuit 22. The BPF amplifier circuit 22 includes an operational amplifier OP1, resistors R1, R2, and R3, capacitors C1 and C2, and a transistor Q1. The drive supply voltage Vc is applied to the operational amplifier OP1 as a bias voltage. The non-inverting input terminal of the operational amplifier OP1 is grounded. The inverting input terminal of the operational amplifier OP1 is connected through the capacitor C1 to the first end of the resistor R1. The second end of the resistor R1 is connected to the output terminal of the LPF differential amplifier circuit 21. The node at which the resistor R1 and the capacitor C1 are connected to each other is connected through the resistor R2 to the drain of the transistor Q1. The source of the transistor Q1 is grounded. The gate of the transistor Q1 is connected to the control circuit 13. The output terminal of the operational amplifier OP1 is connected to the input terminal of the comparator 23, connected through the resistor R3 to the node at which the capacitor C1 and the inverting input terminal of the operational amplifier OP1 are connected to each other, and connected through the capacitor C2 to the node at which the resistor R1 and the capacitor C1 are connected to each other. When the transistor Q1 is operated under the condition in which the drain and the source of the transistor Q1 are not short-circuited, the resistor R2 is dispensable.

The BPF amplifier circuit 22 serves as an amplifier circuit and also serves as a band pass filter. The center frequency fc1 of the band pass filter in the BPF amplifier circuit 22 is represented by Equation (1).

[Math 1]

$$fc1 = \frac{1}{2\pi} \sqrt{\frac{1}{R3C1C2} \left( \frac{1}{R1} + \frac{1}{R2 + Rds} \right)} \quad (1)$$

Here, R1, R2, and R3 denote the resistances of the resistors R1, R2, and R3, respectively, and C1 and C2 denote the capacitances of the capacitors C1 and C2, respectively. Rds denotes the resistance between the drain and the source of the transistor Q1.

Figure 3A:
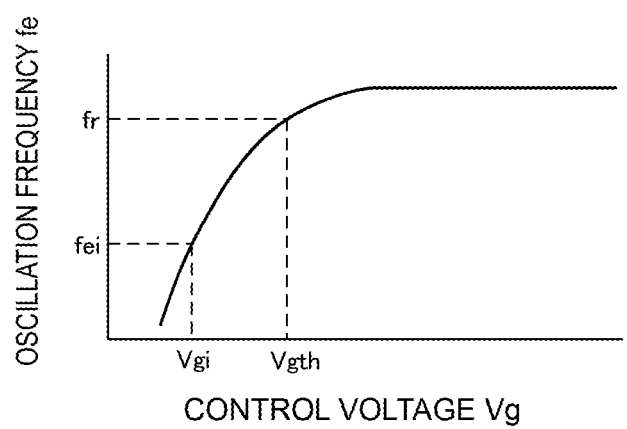
FIG. 3A is a graph illustrating a variation in oscillation frequency fe with respect to a variation in control voltage Vg.

FIG. 3A is a graph illustrating a variation in the oscillation frequency fe with respect to a variation in the control voltage Vg. The drive supply voltage Vc is maintained at a fixed level. As the control voltage Vg gradually increases, starting from a state in which the control voltage Vg is not applied to the gate of the transistor Q1, the drain current of the transistor Q1 increases, and thus the resistance between the drain and the source of the transistor Q1 decreases. In short, the resistance (impedance) between the drain and the source of the transistor Q1 varies depending on the control voltage Vg. Consequently, as can be seen from Equation (1), the center frequency fc1 of the BPF amplifier circuit 22 increases. In other words, the bandpass characteristics of the BPF amplifier circuit 22 change as the resistance (impedance) between the drain and the source of the transistor Q1 varies. As a result, the oscillation frequency fe of the self oscillation circuit 20 increases. As the control voltage Vg further increases, the resistance between the drain and the source of the transistor Q1 further decreases. Consequently, as can be seen from Equation (1), the center frequency fc1 of the BPF amplifier circuit 22 becomes substantially fixed. As a result, the oscillation frequency fe of the self oscillation circuit 20 becomes substantially fixed.

In this way, the oscillation frequency fe of the self oscillation circuit 20 varies depending on the control voltage Vg. This situation can also be described as follows. The phase characteristics of the BPF amplifier circuit 22 change as the resistance between the drain and the source of the transistor Q1 varies depending on the control voltage Vg. As a result, in accordance with the Barkhausen condition for oscillation, which states that a signal is subjected to a phase change of an integer multiple of 360 (deg) after going around an oscillation loop, the phase difference between the input and the output (hereinafter referred to as an input-output phase difference) of the piezoelectric pump 11, which is generated from the input signal and the output signal used for driving the piezoelectric pump 11, varies so as to offset the change in the phase characteristics of the BPF amplifier circuit 22. Consequently, the drive frequency of the piezoelectric pump 11 varies, and thus the oscillation frequency fe of the self oscillation circuit 20 varies.

In more detail, the Barkhausen condition for oscillation is composed of the following two equations.

[Math 2]

$$G \geq 0 (\text{dB}) \quad (2.1)$$

$$P = \sum_{i=1}^{x} \theta_i = 360n(\text{deg}) \quad (2.2)$$

Here, G denotes the gain after a signal goes around an oscillation loop, and Equation (2.1) indicates that the loop gain is equal to or more than 0 dB.

Figure 4A:
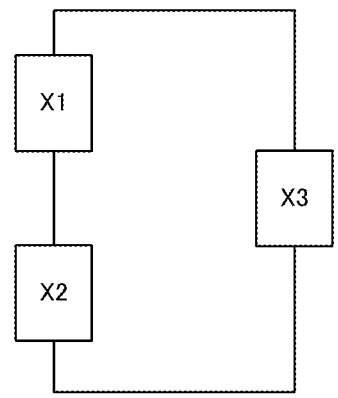
FIG. 4A is a block diagram illustrating an example of an oscillation circuit.

In addition, Equation (2.2) indicates that the phase change after a signal goes around an oscillation loop is an integer multiple of 360 (deg) and indicates that, for example, the total of the phase differences $\theta_i$ (i=1, . . . , x) is an integer multiple of 360 (deg), where $\theta_i$ is an input-output phase difference of each block included in an oscillation circuit formed by x blocks. Here, n is an integer. In FIG. 4A, an oscillation circuit formed by, for example, three blocks X1, X2, and X3 is illustrated.

In the fluid control device 10 illustrated in FIG. 1, the input-output phase difference of the inverting comparator 24 needs to be 180 (deg). Accordingly, if the input-output phase difference of the resistor for detecting output current R0 is $\theta a$ (deg), the input-output phase difference of the piezoelectric element 12, that is, the input-output phase difference of the piezoelectric pump 11, is 180−$\theta a$ (deg).

Further, in accordance with Equation (2.2), the input-output phase difference of the loop formed by the LPF differential amplifier circuit 21, the BPF amplifier circuit 22, the comparator 23, and the resistor for detecting output current R0 is an integer multiple of 360 (deg). If the input-output phase difference of the LPF differential amplifier circuit 21 and the input-output phase difference of the comparator 23 are both equal to 180 (deg) and the input-output phase difference of the BPF amplifier circuit 22 is $\theta b$ (deg), the input-output phase difference of the resistor for detecting output current R0 is −$\theta b$+360n (deg).

In summary, the input-output phase difference of the BPF amplifier circuit 22 varies as the control voltage Vg is varied, and the input-output phase difference of the resistor for detecting output current R0 varies so as to offset the variation in the input-output phase difference of the BPF amplifier circuit 22. As a result, the input-output phase difference of the piezoelectric pump 11 varies.

Figure 4B:
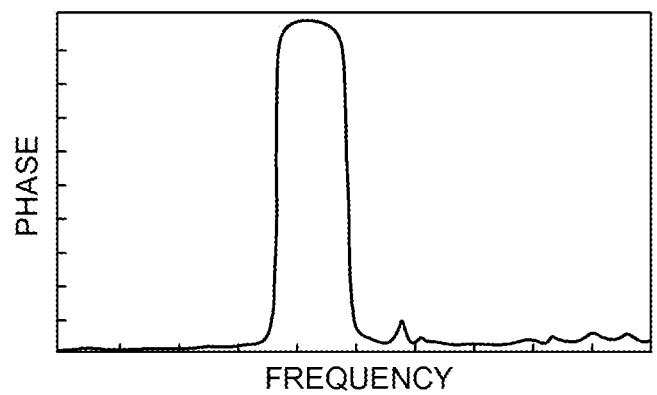
FIG. 4B is a graph illustrating an example of a variation in the phase of the impedance of a piezoelectric element with respect to a variation in frequency.

Further, as can be seen from an example of the impedance phase characteristics of the piezoelectric element 12 illustrated in FIG. 4B, the input-output phase difference of the piezoelectric pump 11 varies depending on the frequency, and thus the drive frequency of the piezoelectric pump 11 varies so as to satisfy Equation (2.2), leading to a variation in the oscillation frequency fe.

Figure 3B:
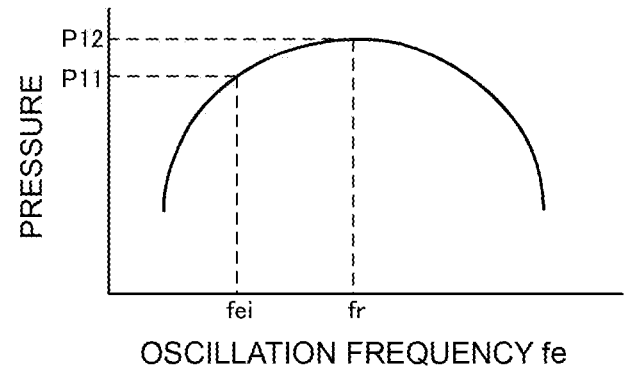
FIG. 3B is a graph illustrating a variation in pressure with respect to a variation in oscillation frequency fe in the case where a piezoelectric pump 11 operates at a fixed flow rate.

FIG. 3B is a graph illustrating the variation in pressure with respect to the variation in oscillation frequency fe in the case where the piezoelectric pump 11 operates at a fixed flow rate. Here, the drive supply voltage Vc is maintained at a fixed level. The pressure obtained in the case where the piezoelectric pump 11 operates at a fixed flow rate is the pressure of the piezoelectric pump 11 obtained in the case where the flow rate of the piezoelectric pump 11 is maintained at a fixed level. The pressure of the piezoelectric pump 11 is a difference obtained by subtracting the suction pressure of the piezoelectric pump 11 from the discharge pressure of the piezoelectric pump 11. The flow rate of the piezoelectric pump 11 is a rate of the flow from the suction port to the discharge port of the piezoelectric pump 11. The variation in the pressure of the piezoelectric pump 11 with respect to the variation in the oscillation frequency fe has a single peak. The pressure of the piezoelectric pump 11 reaches the maximum when the oscillation frequency fe is approximately equal to the resonant frequency fr of the piezoelectric element 12.

As illustrated in FIG. 3A, the self oscillation circuit 20 is set so that the oscillation frequency fe is approximately equal to the resonant frequency fr of the piezoelectric element 12 when the control voltage Vg is equal to the threshold Vgth. At this time, the BPF amplifier circuit 22 is set so that the center frequency fc1 is approximately equal to the resonant frequency fr of the piezoelectric element 12 when the control voltage Vg is equal to the threshold Vgth. Consequently, when the control voltage Vg is equal to the threshold Vgth, the efficiency of the fluid control device 10 is high. Here, the efficiency of the fluid control device 10 is given by the discharge pressure output of the piezoelectric pump 11 with respect to the electric power that is input to the fluid control device 10.

As illustrated in FIG. 3A, as the control voltage Vg increases from Vgi, the oscillation frequency fe gradually increases from fei. Here, the control voltage Vgi is lower than the threshold Vgth. As illustrated in FIG. 3B, as the oscillation frequency fe increases from fei, the pressure of the piezoelectric pump 11 gradually increases from P11. As illustrated in FIG. 3A and FIG. 3B, when the control voltage Vg reaches the threshold Vgth, the oscillation frequency fe becomes approximately equal to the resonant frequency fr of the piezoelectric element 12, and the pressure of the piezoelectric pump 11 reaches P12. The pressure P12 is the maximum pressure of the piezoelectric pump 11 obtained when the oscillation frequency fe is varied while the drive supply voltage Vc is maintained at a fixed level. The control voltage Vg may gradually be decreased from a higher voltage level than the threshold Vgth so as to gradually increase the pressure of the piezoelectric pump 11.

Figure 5:
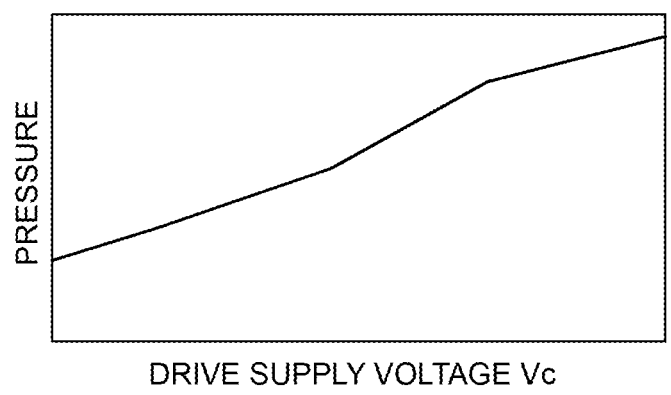
FIG. 5 is a graph illustrating a variation in pressure with respect to a variation in drive supply voltage Vc in the case where the piezoelectric pump 11 operates at a fixed flow rate.

FIG. 5 is a graph illustrating a variation in pressure with respect to a variation in the drive supply voltage Vc in the case where the piezoelectric pump 11 operates at a fixed flow rate. Here, the control voltage Vg is maintained at a fixed level. The drive supply voltage Vc and the pressure of the piezoelectric pump 11 is substantially proportional when the drive supply voltage is in a normal range used for driving a piezoelectric pump.

Figure 6:
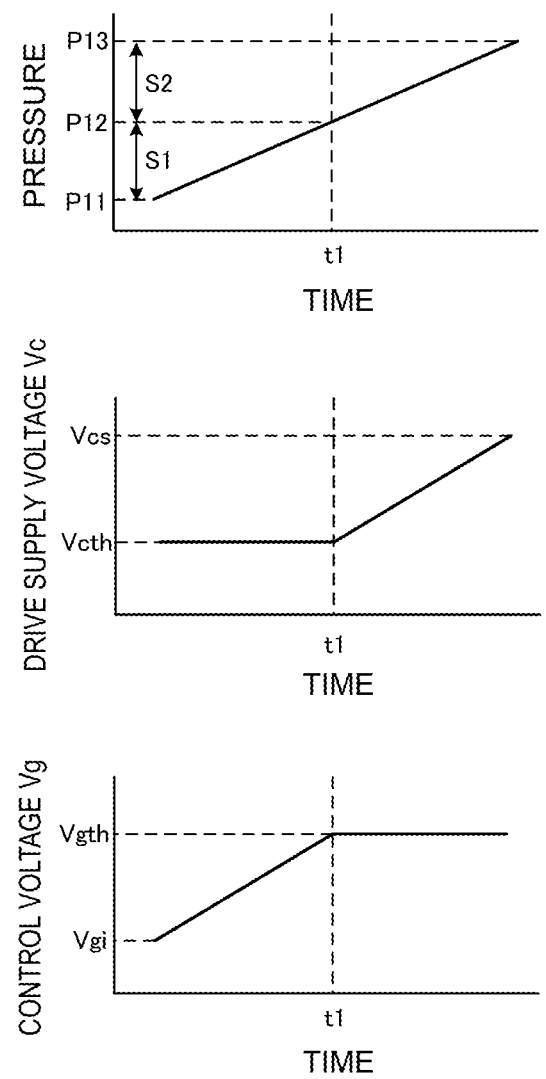
FIG. 6 illustrates a variation in pressure, a variation in drive supply voltage Vc, and a variation in control voltage Vg as time passes in the case where the piezoelectric pump 11 operates at a fixed flow rate in the fluid control device 10.

FIG. 6 illustrates a variation in the pressure, a variation in the drive supply voltage Vc, and a variation in the control voltage Vg as time passes in the case where the piezoelectric pump 11 operates at a fixed flow rate in the fluid control device 10. From the startup to the time point t1, the control voltage Vg is gradually increased from Vgi to the threshold Vgth while the drive supply voltage Vc is maintained at the threshold Vcth. The threshold Vcth is the lower voltage limit of the drive supply voltage Vc at which the self oscillation circuit 20 is operable. This increase in the control voltage Vg causes the pressure of the piezoelectric pump 11 to gradually increase from P11 to P12. After the time point t1, the drive supply voltage Vc is gradually increased from the threshold Vcth to Vcs while the control voltage Vg is maintained at the threshold Vgth. This increase in the drive supply voltage Vc causes the pressure of the piezoelectric pump 11 to gradually increase from P12 to P13. Consequently, the pressure of the piezoelectric pump 11 gradually increases over a wide range of pressure.

An output range S1 of the discharge pressure of the piezoelectric pump 11 from the pressure P11 to the pressure P12 is an example of a "first low-output region" according to the present disclosure. An output range S2 of the discharge pressure of the piezoelectric pump 11 from the pressure P12 to the pressure P13 is an example of a "first high-output region" according to the present disclosure. The upper limit of the output range S2 (pressure P13) is higher than the upper limit of the output range S1 (pressure P12), and the lower limit of the output range S2 (pressure P12) is higher than the lower limit of the output range S1 (pressure P11). The control circuit 13 varies in the output range S1 the control voltage Vg while maintaining the drive supply voltage Vc at a fixed level and varies in the output range S2 the drive supply voltage Vc while maintaining the control voltage Vg at a fixed level.

Figure 7:
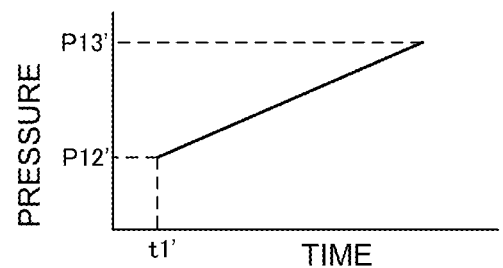
FIG. 7 illustrates a variation in pressure and a variation in drive supply voltage Vc as time passes in the case where the piezoelectric pump operates at a fixed flow rate in a fluid control device according to a comparative example.
Figure 7:
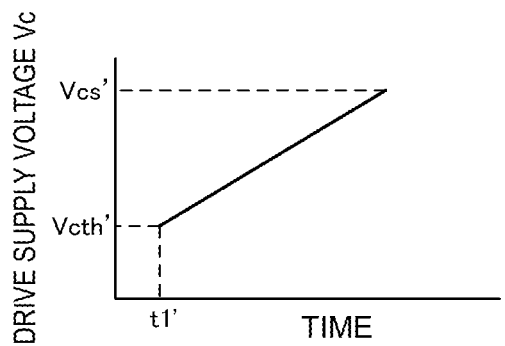

FIG. 7 illustrates a variation in the pressure and a variation in the drive supply voltage Vc as time passes in the case where a piezoelectric pump operates at a fixed flow rate in a fluid control device according to a comparative example. In the fluid control device according to the comparative example, when the drive supply voltage Vc is gradually increased from Vcth' to Vcs', the pressure of the piezoelectric pump gradually increases from P12' to P13'. In essence, in the fluid control device according to the comparative example, a change in the drive supply voltage Vc causes the pressure of the piezoelectric pump to vary in the entire output range of the discharge pressure. In other words, the fluid control device according to the comparative example has only the output range corresponding to the output range S2.

The fluid control device according to the comparative example is a pressurizing-type sphygmomanometer. FIG. 7 represents a pressurizing process of the sphygmomanometer during a blood pressure measurement. The pressure P12' denotes the pressure at the time point t1' when the sphygmomanometer according to the comparative example starts to measure a blood pressure, and the pressure is increased at a fixed rate as time passes to a predetermined level equal to the upper limit P13' or less. A blood pressure can be measured by detecting a pulse wave while the pressure is increased to the predetermined level. A blood pressure cannot be measured at a pressure equal to P12' or less.

In the first embodiment, the discharge pressure output of the piezoelectric pump 11 is varied by shifting the oscillation frequency fe of the self oscillation circuit 20 from the resonant frequency fr of the piezoelectric element 12 while the drive supply voltage Vc is maintained at the lower voltage limit (threshold Vcth). In this way, the piezoelectric pump 11 operates in a low output range of the discharge pressure. The discharge pressure output of the piezoelectric pump 11 is varied not only by varying the oscillation frequency fe but also by varying the drive supply voltage Vc in a range whose lower end is equal to the lower voltage limit while the oscillation frequency fe is maintained at a frequency approximately equal to the resonant frequency fr.

In this way, the output range of the discharge pressure of the piezoelectric pump 11, that is, the dynamic range of the piezoelectric pump 11 is enlarged. The upper limit of the discharge pressure output of the piezoelectric pump 11 in the case where the oscillation frequency fe is varied equals the lower limit of the discharge pressure output of the piezoelectric pump 11 in the case where the drive supply voltage Vc is varied. In this way, the discharge pressure output of the piezoelectric pump 11 can continuously be varied in the entire output range of the discharge pressure of the piezoelectric pump 11.

Second Embodiment

Figure 8:
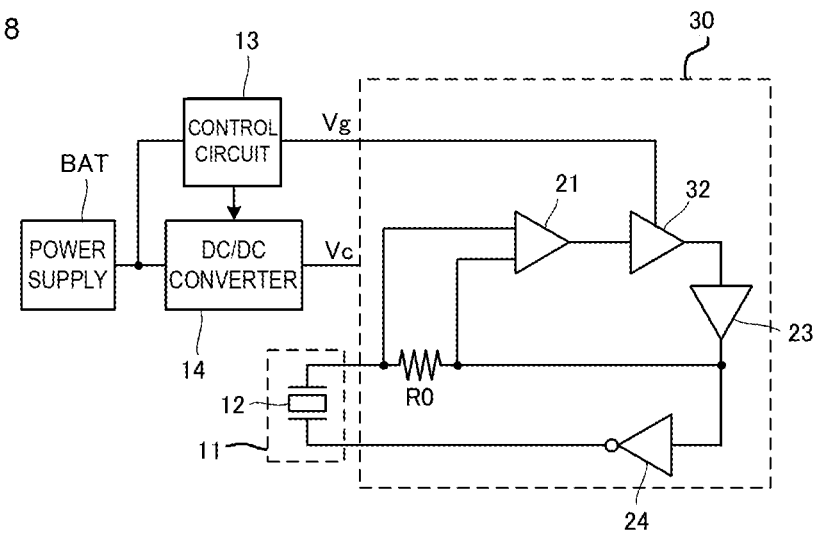
FIG. 8 is a block diagram illustrating a configuration of a fluid control device according to a second embodiment.

In a second embodiment, a control voltage applied to a varicap causes the discharge pressure output of a piezoelectric pump to vary. FIG. 8 is a block diagram illustrating a configuration of a fluid control device according to the second embodiment. The fluid control device according to the second embodiment includes a self oscillation circuit 30 in which a BPF amplifier circuit 32 is included.

Figure 9:
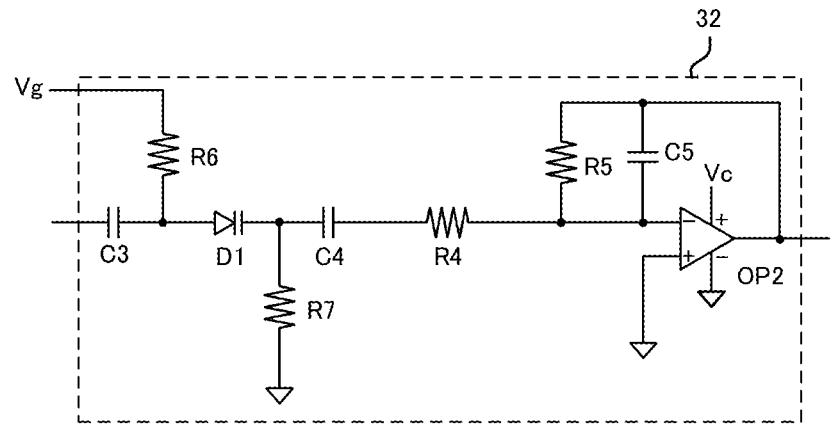
FIG. 9 is a circuit diagram of an amplifier circuit having a BPF 32.

FIG. 9 is a circuit diagram of the BPF amplifier circuit 32. The BPF amplifier circuit 32 includes an operational amplifier OP2, resistors R4, R5, R6, and R7, capacitors C3, C4, and C5, and a varicap D1. The varicap D1 is an example of a "variable impedance unit" and a "variable capacitance element" of the present disclosure. The drive supply voltage Vc is applied to the operational amplifier OP2 as a bias voltage. The non-inverting input terminal of the operational amplifier OP2 is grounded. The inverting input terminal of the operational amplifier OP2 is connected through the resistor R4 to the first end of the capacitor C4. The second end of the capacitor C4 is connected to the cathode of the varicap D1. The anode of the varicap D1 is connected through the capacitor C3 to the output terminal of the LPF differential amplifier circuit 21. The node at which the capacitor C3 and the varicap D1 are connected to each other is connected through the resistor R6 to the control circuit 13. The control circuit 13 applies the control voltage Vg to the anode of the varicap D1. The node at which the varicap D1 and the capacitor C4 are connected to each other is grounded through the resistor R7. Each of the resistances of the resistors R6 and R7 is set to a value sufficiently larger than the absolute values of the impedances of other elements. The output terminal of the operational amplifier OP2 is connected to the input terminal of the comparator 23 and connected through a parallel circuit formed by the resistor R5 and the capacitor C5 to the node at which the resistor R4 and the inverting input terminal of the operational amplifier OP2 are connected to each other.

The BPF amplifier circuit 32, which has the above circuit configuration, serves as an amplifier circuit and also serves as a band pass filter. The center frequency fc2 of the band pass filter in the BPF amplifier circuit 32 is represented by Equation (3).

[Math 3]

$$fc2 = \frac{CmR4 + C5R5}{4\pi CmR4C5R5} = \frac{1}{4\pi C5R5} + \frac{1}{4\pi R4}\left(\frac{1}{C3} + \frac{1}{C4} + \frac{1}{Cd}\right) \quad (3)$$

Here, R4 and R5 denote the resistances of the resistors R4 and R5, respectively, and C3, C4, and C5 denote the capacitances of the capacitors C3, C4, and C5, respectively. Cd denotes the capacitance of the varicap D1. Cm denotes the combined capacitance of the capacitances of the capacitor C3, the capacitor C4, and the varicap D1 and is represented by Cm=C3C4Cd/(C3C4+C4Cd+CdC3).

As the control voltage Vg gradually increases in the negative direction, starting from a state in which the control voltage Vg is not applied to the varicap D1, the reverse voltage applied to the varicap D1 increases, and thus the capacitance of the varicap D1 decreases. In short, the capacitance of the varicap D1 varies depending on the control voltage Vg. In other words, the impedance of the varicap D1 varies depending on the control voltage Vg. Consequently, as can be seen from Equation (3), the center frequency fc2 of the BPF amplifier circuit 32 increases. As a result, the oscillation frequency fe of the self oscillation circuit 30 increases. In other words, the bandpass characteristics of the BPF amplifier circuit 32 change as the impedance of the varicap D1 varies. The self oscillation circuit 30 is set so that the oscillation frequency fe is approximately equal to the resonant frequency fr of the piezoelectric element 12 when the control voltage Vg is equal to the threshold Vgth. Accordingly, as can be seen from FIG. 3B, as the control voltage Vg increases in the negative direction from a smaller voltage than the threshold Vgth, the discharge pressure output of the piezoelectric pump 11 gradually increases.

In the second embodiment, the piezoelectric pump 11 can also be operated in a low output range of the discharge pressure by shifting the oscillation frequency fe of the self oscillation circuit 30 from the resonant frequency fr of the piezoelectric element 12.

Figure 10:
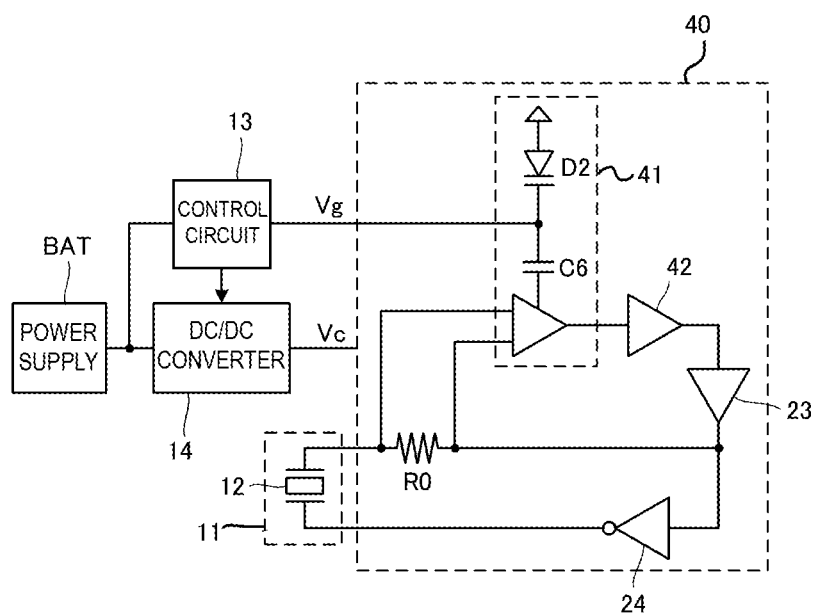
FIG. 10 is a block diagram illustrating a configuration of a fluid control device according to a modification of the second embodiment.

Next, a fluid control device according to a modification of the second embodiment will be described. In the modification of the second embodiment, the LPF differential amplifier circuit includes a varicap. FIG. 10 is a block diagram illustrating a configuration of the fluid control device according to the modification of the second embodiment. The fluid control device according to the modification of the second embodiment includes a self oscillation circuit 40 in which an LPF differential amplifier circuit 41 and a BPF amplifier circuit 42 are included. The LPF differential amplifier circuit 41 is an example of a "filter circuit" and a "low pass filter" according to the present disclosure. The LPF differential amplifier circuit 41 includes a varicap D2 and a capacitor C6. The control circuit 13 applies the control voltage Vg to the cathode of the varicap D2 and thus changes the bandpass characteristics of the LPF differential amplifier circuit 41. The BPF amplifier circuit 42 has a circuit configuration similar to, for example, the circuit configuration of the BPF amplifier circuit 32 (refer to FIG. 9). However, the BPF amplifier circuit 42 is not connected to the control circuit 13 and does not include the resistor R6, and the varicap D1 is replaced by a capacitor whose capacitance does not vary. Consequently, the center frequency of the band pass filter in the BPF amplifier circuit 42 is maintained at a fixed value.

Figure 11:
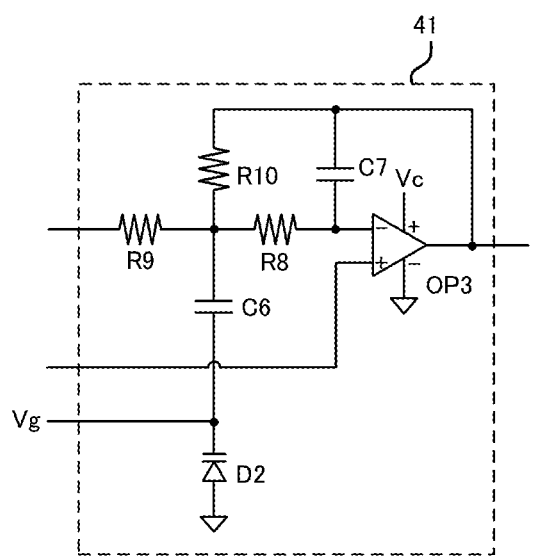
FIG. 11 is a circuit diagram of a differential amplifier circuit having a low pass filter (LPF) 41.

FIG. 11 is a circuit diagram of the LPF differential amplifier circuit 41. The LPF differential amplifier circuit 41 includes an operational amplifier OP3, resistors R8, R9, and R10, capacitors C6 and C7, and a varicap D2. The drive supply voltage Vc is applied to the operational amplifier OP3 as a bias voltage. The non-inverting input terminal of the operational amplifier OP3 is connected to the first end of the resistor for detecting output current R0 (a terminal of the resistor for detecting output current R0, the terminal being connected to the output terminal of the comparator 23). The inverting input terminal of the operational amplifier OP3 is connected through the resistor R8 to the first end of the resistor R9. The second end of the resistor R9 is connected to the second end of the resistor for detecting output current R0 (a terminal of the resistor for detecting output current R0, the terminal being connected to the piezoelectric element 12). The node at which the resistor R8 and the resistor R9 are connected to each other is connected through the capacitor C6 to the cathode of the varicap D2. The cathode of the varicap D2 is connected to the control circuit 13. The control circuit 13 applies the control voltage Vg to the cathode of the varicap D2. The anode of the varicap D2 is grounded. The output terminal of the operational amplifier OP3 is connected to the input terminal of the BPF amplifier circuit 42, connected through the capacitor C7 to the node at which the resistor R8 and the inverting input terminal of the operational amplifier OP3 are connected to each other, and connected through the resistor R10 to the node at which the resistor R8 and the resistor R9 are connected to each other. The LPF differential amplifier circuit 41, which has the above circuit configuration, serves as a differential amplifier circuit and also serves as a low pass filter.

As the control voltage Vg varies, the reverse voltage applied to the varicap D2 varies, and thus the capacitance of the varicap D2 varies. Consequently, the bandpass characteristics of the low pass filter in the LPF differential amplifier circuit 41 change, and thus the oscillation frequency fe of the self oscillation circuit 40 varies. As a result, the discharge pressure output of the piezoelectric pump 11 varies.

In the modification of the second embodiment, the piezoelectric pump 11 can also be operated in a low output range of the discharge pressure by shifting the oscillation frequency fe from the resonant frequency fr of the piezoelectric pump 11.

Third Embodiment

Figure 12:
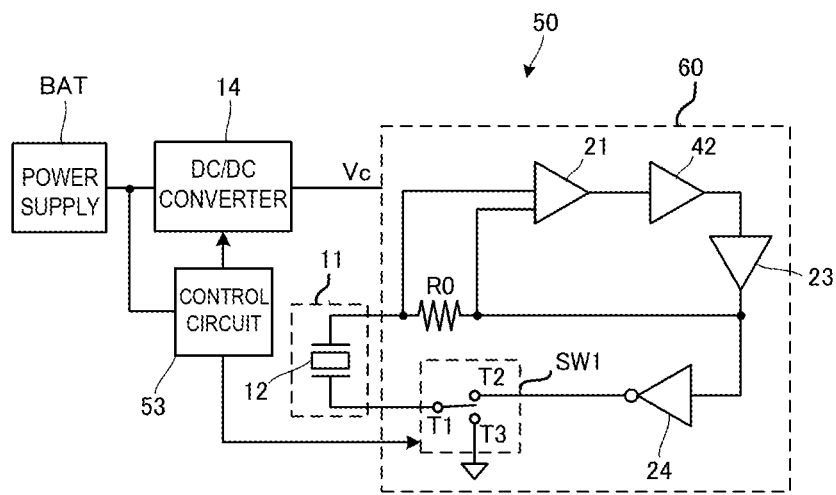
FIG. 12 is a block diagram illustrating a configuration of a fluid control device 50 according to a third embodiment.

In a third embodiment, a self-oscillation circuit drives a piezoelectric pump by using an unbalanced signal in a low output range of discharge pressure of the piezoelectric pump. FIG. 12 is a block diagram illustrating a configuration of a fluid control device 50 according to the third embodiment. The fluid control device 50 includes a piezoelectric pump 11, a self-oscillation circuit 60, a control circuit 53, a DC/DC converter 14, and a power supply BAT. The control circuit 53 controls the drive supply voltage Vc and controls switching of a switch SW1 in the self oscillation circuit 60.

The self-oscillation circuit 60 includes a resistor for detecting output current R0, an LPF differential amplifier circuit 21, a BPF amplifier circuit 42, a comparator 23, an inverting comparator 24, and the switch SW1. The output terminal of the comparator 23 is connected through the resistor for detecting output current R0 to a first end of the piezoelectric element 12 and also connected to the input terminal of the inverting comparator 24. The output terminal of the inverting comparator 24 is connected through the switch SW1 to a second end of the piezoelectric element 12. The switch SW1 has terminals T1, T2, and T3. The terminal T1 is connected to the second end of the piezoelectric element 12. The terminal T2 is connected to the output terminal of the inverting comparator 24. The terminal T3 is grounded. The switch SW1 switches between the connection of the terminal T1 to the terminal T2 and the connection of the terminal T1 to the terminal T3 in accordance with the control performed by the control circuit 53. The switch SW1 is formed by an FET switch or the like.

The self-oscillation circuit 60 drives the piezoelectric element 12 by using a balanced signal (drives in a balanced manner) when the terminal T1 and the terminal T2 of the switch SW1 are connected to each other. The self-oscillation circuit 60 drives the piezoelectric element 12 by using an unbalanced signal (drives in an unbalanced manner) when the terminal T1 and the terminal T3 of the switch SW1 are connected to each other. The amplitude of the balanced signal applied to the piezoelectric element 12 is about twice the amplitude of the unbalanced signal applied to the piezoelectric element 12. The self-oscillation circuit 60 is set so that the oscillation frequency fe is approximately equal to the resonant frequency fr of the piezoelectric element 12.

Figure 13:
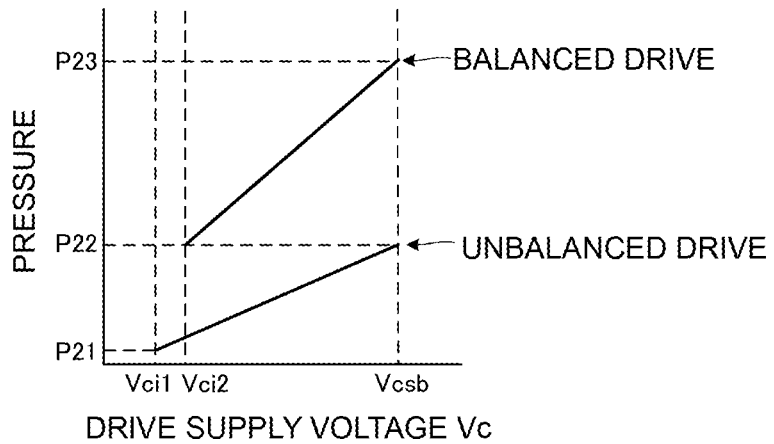
FIG. 13 is a graph illustrating a variation in pressure with respect to a variation in drive supply voltage Vc in the case where the piezoelectric pump 11 operates at a fixed flow rate.

FIG. 13 is a graph illustrating a variation in pressure with respect to a variation in the drive supply voltage Vc in the case where the piezoelectric pump 11 operates at a fixed flow rate. When the piezoelectric element 12 is driven in the unbalanced manner, the pressure of the piezoelectric pump 11 gradually increases from P21 to P22 as the drive supply voltage Vc increases from Vci1 to Vcsb. When the piezoelectric element 12 is driven in the balanced manner, the pressure of the piezoelectric pump 11 gradually increases from P22 to P23 as the drive supply voltage Vc increases from Vci2 to Vcsb. Here, the drive supply voltage Vci2 is about half the drive supply voltage Vcsb. The rate of variation in the pressure of the piezoelectric pump 11 with respect to the drive supply voltage Vc in the balanced drive is about twice the rate of variation in the pressure of the piezoelectric pump 11 with respect to the drive supply voltage Vc in the unbalanced drive.

Figure 14:
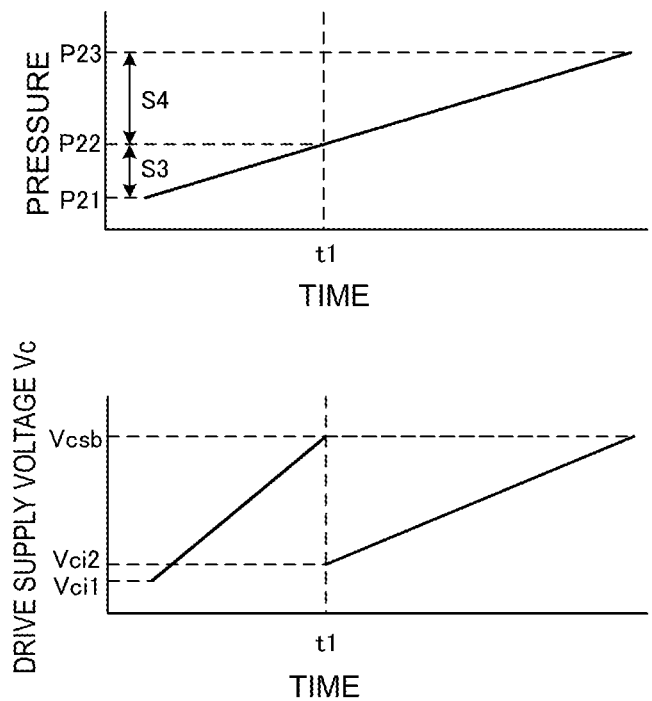
FIG. 14 illustrates a variation in pressure and a variation in drive supply voltage Vc as time passes in the case where the piezoelectric pump 11 operates at a fixed flow rate.

FIG. 14 illustrates a variation in pressure and a variation in drive supply voltage Vc as time passes in the case where the piezoelectric pump 11 operates at a fixed flow rate. From the startup to the time point t1, the drive supply voltage Vc is gradually increased from Vci1 to Vcsb while the terminal T1 of the switch SW1 is grounded and the piezoelectric element 12 is driven in the unbalanced manner. This increase in the drive supply voltage Vc causes the pressure of the piezoelectric pump 11 to gradually increase from P21 to P22. After the time point t1, the drive supply voltage Vc is gradually increased from Vci2 to Vcsb while the terminal T1 of the switch SW1 is connected to the inverting comparator 24 and the piezoelectric element 12 is driven in the balanced manner. This increase in the drive supply voltage Vc causes the pressure of the piezoelectric pump 11 to gradually increase from P22 to P23. At this time, the amount of variation in the drive supply voltage Vc per unit time in the balanced drive is set to about half the amount of variation in the drive supply voltage Vc per unit time in the unbalanced drive. This setting enables the amount of variation in the pressure of the piezoelectric pump 11 per unit time (pressurizing rate) to be substantially fixed. Consequently, the pressure of the piezoelectric pump 11 gradually increases over a wide range of pressure from the pressure P21 to the pressure P23.

An output range S3 of the discharge pressure of the piezoelectric pump 11 from the pressure P21 to the pressure P22 is an example of a "second low-output region" according to the present disclosure. An output range S4 of the discharge pressure of the piezoelectric pump 11 from the pressure P22 to the pressure P23 is an example of a "second high-output region" according to the present disclosure. The upper limit of the output range S4 (pressure P23) is higher than the upper limit of the output range S3 (pressure P22), and the lower limit of the output range S4 (pressure P22) is higher than the lower limit of the output range S3 (pressure P21). The control circuit 53 drives the piezoelectric element 12 by using the unbalanced signal in the output range S3 and drives the piezoelectric element 12 by using the balanced signal in the output range S4.

In the third embodiment, the amplitude of the drive voltage applied to the piezoelectric element 12 is reduced by driving the piezoelectric element 12 in the unbalanced manner. In this way, the piezoelectric pump 11 operates in a low output range of the discharge pressure. In addition, the balanced drive and the unbalanced drive are switched depending on the output range of the discharge pressure of the piezoelectric pump 11. In this way, the output range of the discharge pressure of the piezoelectric pump 11, that is, the dynamic range of the piezoelectric pump 11 is enlarged. Further, since the oscillation frequency fe of the self-oscillation circuit 60 is approximately equal to the resonant frequency fr of the piezoelectric element 12 in the entire output range of the discharge pressure of the piezoelectric pump 11, the fluid control device 50 is highly efficient. Consequently, if the power supply BAT is constituted by a battery, the life of the battery is extended.

The fluid control device 50 according to the third embodiment may be combined with the fluid control device 10 according to the first embodiment. Specifically, the BPF amplifier circuit 42 (refer to FIG. 12) may be replaced by the BPF amplifier circuit 22 (refer to FIG. 1), and the configuration of the fluid control device 50 may be modified so that the control circuit 53 controls the gate voltage of the transistor Q1 in the BPF amplifier circuit 22. For example, when the discharge pressure output of the piezoelectric pump 11 is gradually increased, this fluid control device operates as follows. In the first stage, the piezoelectric element 12 is driven in the unbalanced manner, and the control voltage Vg is varied while the drive supply voltage Vc is maintained at the threshold Vcth. In the second stage, the piezoelectric element 12 is driven in the unbalanced manner, and the drive supply voltage Vc is varied while the control voltage Vg is maintained at the threshold Vgth. In the third stage, the piezoelectric element 12 is driven in the balanced manner, and the drive supply voltage Vc is varied while the control voltage Vg is maintained at the threshold Vgth.

Fourth Embodiment

Figure 15:
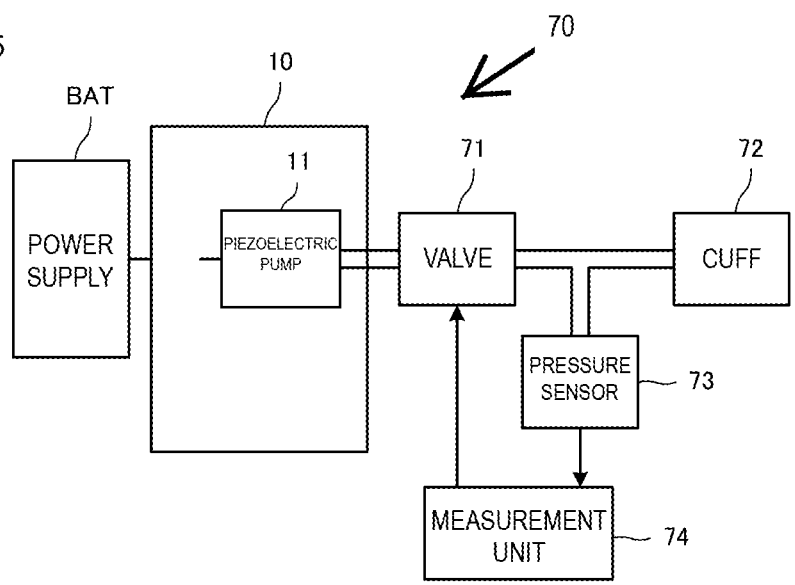
FIG. 15 is a block diagram illustrating a configuration of a sphygmomanometer 70 according to a fourth embodiment.

In a fourth embodiment, a sphygmomanometer will be described. FIG. 15 is a block diagram illustrating a configuration of a sphygmomanometer 70 according to the fourth embodiment. The sphygmomanometer 70 includes a fluid control device 10, a power supply BAT for the fluid control device 10, a valve 71, a cuff 72, a pressure sensor 73, and a measurement unit 74.

The configuration of the fluid control device 10 has been described in the first embodiment. The cuff 72 is coupled through the valve 71 to the discharge port of a piezoelectric pump 11 of the fluid control device 10. The pressure sensor 73 detects the air pressure in the cuff 72. When the piezoelectric pump 11 is to discharge air, the valve 71 allows air to flow into the cuff, and when the air pressure in the cuff is to be reduced, the valve 71 allows air to be released into the air at a predetermined flow rate. During a pressurizing process, the measurement unit 74 detects a pulse wave in accordance with a value detected by the pressure sensor 73 and obtains the maximum blood pressure and the minimum blood pressure by using the oscillometric method. After that, air is released through the valve 71 during a pressure-releasing process. In this way, the total amount of time required for a blood pressure measurement is shortened by using the method to measure a blood pressure during the pressurizing process because air can be released rapidly during the pressure-releasing process after the measurement.

In addition, the amount of current consumption is small because the battery is used only while the pressure is raised. However, the cuff may be pressurized to a predetermined pressure during the pressurizing process, and a blood pressure may be measured during the following pressure-releasing process.

As described above, the piezoelectric pump 11 is operable in a low output range of discharge pressure in the fourth embodiment. Consequently, an accurate blood pressure measurement is possible when the sphygmomanometer 70 is used for a newborn baby. In addition, as described above, the dynamic range of the piezoelectric pump 11 is large, and the discharge pressure output of the piezoelectric pump 11 can continuously be varied. Therefore, an accurate blood pressure measurement is possible in a wide range of blood pressure.

The embodiments described above are illustrative in every respect and are not meant to be limiting. Modifications and variations can be performed as appropriate by those skilled in the art. The scope of the present disclosure is defined not by the embodiments described above but by the claims. Further, modifications that are made to the embodiments within the scope of the claims and equivalents are included within the scope of the present disclosure.

REFERENCE SIGNS LIST

BAT power supply
C1 to C7 capacitor
D1, D2 varicap (variable impedance unit, variable capacitance element)
OP1 to OP3 operational amplifier
Q1 transistor (variable impedance unit, FET)
R0 resistor for detecting output current
R1 to R10 resistor
SW1 switch
T1 to T3 terminal
10, 50 fluid control device
11 piezoelectric pump
12 piezoelectric element
13, 53 control circuit
14 DC/DC converter
20, 30, 40, 60 self-oscillation circuit
21 LPF differential amplifier circuit
22, 32 BPF amplifier circuit (filter circuit, band pass filter)
23 comparator
24 inverting comparator
41 LPF differential amplifier circuit (filter circuit, low pass filter)
42 BPF amplifier circuit
70 sphygmomanometer
71 valve
72 cuff
73 pressure sensor
74 measurement unit

The invention claimed is:

1. A fluid control device comprising:
a piezoelectric pump comprising a piezoelectric element and having a discharge pressure output that varies depending on a drive frequency of the piezoelectric element;
a control circuit configured to generate a control voltage; and
a self-oscillation circuit configured to self-oscillate in accordance with a drive supply voltage and the control voltage, and to drive the piezoelectric element at an oscillation frequency.

2. The fluid control device according to claim 1, wherein a phase difference between signals that drive the piezoelectric pump varies as the control voltage varies.

3. The fluid control device according to claim 2, wherein:
the self-oscillation circuit comprises a filter circuit,
the filter circuit comprises a variable impedance element having an impedance that varies depending on the control voltage, and
a pass band of the filter circuit changes as the impedance of the variable impedance element varies.

4. The fluid control device according to claim 3, wherein the variable impedance element has a resistance or capacitance that varies depending on the control voltage.

5. The fluid control device according to claim 4, wherein:
the variable impedance element comprises a field effect transistor (FET), and
the control voltage is applied to a gate of the FET.

6. The fluid control device according to claim 4, wherein:
the variable impedance element comprises a variable capacitance element, and
the control voltage is applied to the variable capacitance element.

7. The fluid control device according to claim 3, wherein the filter circuit comprises a band pass filter or a low pass filter.

8. The fluid control device according to claim 4, wherein the filter circuit comprises a band pass filter or a low pass filter.

9. The fluid control device according to claim 5, wherein the filter circuit comprises a band pass filter or a low pass filter.

10. The fluid control device according to claim 6, wherein the filter circuit comprises a band pass filter or a low pass filter.

11. The fluid control device according to claim 1, wherein the drive supply voltage is a power supply voltage for the self-oscillation circuit.

12. The fluid control device according to claim 1, wherein:
the discharge pressure output of the piezoelectric pump is within a predetermined low-output region or a predetermined high-output region,
an upper limit of the high-output region is greater than an upper limit of the low-output region, and a lower limit of the high-output region is greater than a lower limit of the low-output region, and
the control circuit is further configured to:
control the drive supply voltage,
when the discharge pressure output of the piezoelectric pump is in the low-output region, vary the control voltage while maintaining the drive supply voltage at a fixed level, and
when the discharge pressure output of the piezoelectric pump is in the high-output region, vary the drive supply voltage while maintaining the control voltage at a fixed level.

13. The fluid control device according to claim 1, wherein:
the discharge pressure output of the piezoelectric pump is within a predetermined low-output region or a predetermined high-output region,
an upper limit of the high-output region is greater than an upper limit of the low-output region, and a lower limit of the high-output region is greater than a lower limit of the low-output region,
when the discharge pressure output of the piezoelectric pump is in the low-output region, the self-oscillation circuit is configured to drive the piezoelectric element with an unbalanced signal, and when the discharge pressure output of the piezoelectric pump is in the high-output region, the self-oscillation circuit is configured to drive the piezoelectric element with a balanced signal.

14. A sphygmomanometer comprising:

a cuff; and the fluid control device of claim 1, the fluid control device being configured to pressurize the cuff.

* * * * *